(12) United States Patent
Ferreira et al.

(10) Patent No.: US 7,166,754 B2
(45) Date of Patent: Jan. 23, 2007

(54) METHODS AND COMPOSITIONS FOR ENANTIOSELECTIVE OXIDATION REACTIONS

(75) Inventors: Eric M. Ferreira, Pasadena, CA (US); Brian M. Stoltz, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 10/091,372

(22) Filed: Mar. 4, 2002

(65) Prior Publication Data

US 2003/0060656 A1  Mar. 27, 2003

Related U.S. Application Data

(60) Provisional application No. 60/274,642, filed on Mar. 12, 2001.

(51) Int. Cl.
*C07C 27/10* (2006.01)
*C07C 29/00* (2006.01)
*C07C 33/18* (2006.01)

(52) U.S. Cl. ....................... 568/815; 568/715
(58) Field of Classification Search ............... 568/815, 568/715
See application file for complete search history.

(56) References Cited

U.S. PATENT DOCUMENTS

| 5,981,783 | A  |   | 11/1999 | Polt |
| 6,184,381 | B1 | * | 2/2001 | Ikariya et al. ............. 546/136 |
| 6,350,916 | B1 | * | 2/2002 | Guram et al. ............... 568/320 |

OTHER PUBLICATIONS

Yasuhiro Uozumi, Kazuhiko Kato, and Tamio Hayashi☐☐J.Am. Chem.Soc. 1997, 119,5063-5064.*
Takahiro Hosokawa, Tetsuyuki Uno, Shiro Inui and Shun-Ichi Murahashi☐☐J. Am. Chem. Soc. 1981,103,2318-2323.*
Ait-Mohand et al. (1995), "Palladium(II)-Mediated Oxidation of Alcohols Using 1,2-Dichloroethane as Pd(0) Reoxidant," *Tetrahedron Letters* 36(14):2473-2476.
Blackburn et al. (1977), "Homogeneous Catalytic Oxidation of Secondary Alcohols to Ketones by Molecular Oxygen Under Mild Conditions," *J. Chem. Soc. Chem. Commun.*, pp. 157-158.
Hashiguchi et al. (1997), "Kinetic Resolution of Racemic Secondary Alcoholsby Ru$^{II}$-Catalyzed Hydrogen Transfer," *Angew. Chem. Int. Ed. Engl.* 36(3):288-290.
Jensen et al. (2001), "Palladium-Catalyzed Enantioselective Oxidations of Alcohols Using Molecular Oxygen," *J. Am. Chem. Soc.* 123(30):7475-7476.
Nagashima et al. (1981), "Activation of Polyhaloalkanes by Palladium Catalyst. Palladium Catalyzed Oxidation of Alcohols to Carbonyl Compounds with Carbon Tetrachloride," *Chemistry Letters*, pp. 1171-1172.
Nishimura et al. (1999), "Palladium(II)-Catalyzed Oxidation of Alcohols to Aldehydes and Ketones by Molecular Oxygen," *J. Org. Chem.* 64(18):6750-6755.

Peterson et al. (1998), "Palladium-Catalyzed Oxidation of Primary and Secondary Allylic and Benzylic Alcohols," *J. Org. Chem.* 63(10):3185-3189.
Rychnovsky et al. (1996), "Enantioselective Oxidation of Secondary Alcohols Using a Chiral Nitroxyl (N-Oxoammonium Salt) Catalyst," *J. Org. Chem.* 61(4):1194-1195.
Smidt (1962), "Oxidation of Olefins with Palladium Chloride Catalysts," *Chemistry and Industry*, pp. 54-61.
Smidt et al. (1959), "Katalytische Umsetzungen von Olefinen an Platinmetall-Verbindungen," *Angew. Chem.* 71(5):176-182.
Smidt et al. (1962), "The Oxidation of Olefins with Palladium Chloride Catalysts," *Angew. Chem. Internat. Edit. Engl.* 1(2):80-88.
Stahl et al. (2001), "Oxygenation of Nitrogen-Coordinated Palladium(0): Synthetic, Structural, and Mechanistic Studies and Implications for Aerobic Oxidation Catalysis," *J. Am. Chem. Soc.* 123(29):7188-7189.
Steinhoff et al. (2002), "Mechanistic Study of Alcohol Oxidation by the Pd(OAc)$_2$/O$_2$/DMSO Catalyst System and Implications for the Development of Improved Aerobic Oxidation Catalysts," *J. Am. Chem. Soc.* 124(5):766-767.
Tamaru et al. (1979), "Palladium Catalyzed Oxidations of Secondary Alcohols," *Tetrahedron Letters* 20(16):1401-1404.
ten Brink et al. (2000), "Green, Catalytic Oxidation of Alcohols in Water," *Science* 287:1636-1639.
Uozumi et al. (1998), "Cationic Palladium/Boxax Complexes for Catalytic Asymmetric Wacker-Type Cyclization," *J. Org. Chem.* 63(15):5071-5075.
Ferreira et al. (2001), "The Palladium-Catalyzed Oxidative Kinetic Resolution of Secondary Alcohols with Molecular Oxygen," *J. Am. Chem. Soc.* 123(31):7725-7726.
Ferreira et al. (2001), "Palladium-Catalyzed Oxidative Kinetic Resolution of Secondary Alcohols," *Chemtracts-Organic Chemistry*, pp. 654-658.
Hosokawa et al. (1981), "Palladium(II)-Catalyzed Asymmetric Oxidative Cyclization of 2-Allylphenols in the Presence of Copper(II) Acetate and Molecular Oxygen. Study of the Catalysis of the Wacker-Type Oxidation," *J. Am. Chem. Soc.* 103(9):2318-2323.
Kashiwagi et al. (1996), "Enantioselective Electrocatalytic Oxidation of Racemic Alcohols on a TEMPO-Modified Graphite Felt Electrode by Use of Chiral Base (TEMPO=2,2,6,6-tetramethylpiperidin-1-yloxyl)," *Chem. Commun.*, pp. 2745-2746.
Masutani et al. (2000), "Catalytic Asymmetric and Chemoselective Aerobic Oxidation: Kinetic Resolution of Sec-Alcohols," *Tetrahedron Letters* 41:5119-5123.
Togni et al. (1990), "74. Synthesis, Structure, and 2 D-NMR Studies of Novel Chiral ($\eta^3$-Allyl)palladium(II) Complexes Containing the Bidentate Ligand Sparteine," *Helvetica Chimica Acta* 73:723-732.

(Continued)

*Primary Examiner*—Samuel A Barts
*Assistant Examiner*—Lalitha Nagubandi
(74) *Attorney, Agent, or Firm*—Mintz Levine Ferris Glovsky and Popeo, P.C.

(57) ABSTRACT

This invention provides methods and catalyst systems for catalyzing enantioselective oxidation reactions, including cyclization reactions and enantioselective oxidation reactions of secondary alcohols and other similarly reactive organic substrates. Use of the methods and catalyst systems for kinetic resolution of racemic mixtures of secondary alcohols is also described.

28 Claims, No Drawings

OTHER PUBLICATIONS

Trost et al. (1973), "New Synthetic Reactions. Asymmetric Induction in Allylic Alkylations," *J. Am. Chem. Soc.* 95(24):8200-8201.

Uozumi et al. (1997), "Catalytic Asymmetric Wacker-Type Cyclization," *J. Am. Chem. Soc.* 119(21):5063-5064.

Ouzumi et al. (1999), "Design and Preparation of 3,3'-Disubstituted 2,2'-Bis(oxazolyl)-1,1'-binaphthyls (boxax): New Chiral Bis(oxazoline) Ligands for Catalytic Asymmetric Wacker-Type Cyclization," *J. Org. Chem.* 64(5):1620-1625.

Kang et al. (1994), "(-)-α-Isosparteine as a Chiral Ligand in Asymmetric Allylic Alkylation," *Tetrahedron: Asymmetry* 5(7):1347-1352 (abstract only).

Lee et al. (1999), "C2-Symmetric Bisphosphinobioxazoline as a Chiral Ligand. Highly Enantioselective Palladium-Catalyzed Allylic Substitutions and Formation of P,N,N,P Tetradentate Palladium(II) Complexes," *Journal of Organic Chemistry* 64(12):4445-4451 (abstract only).

Norrby et al. (1993), "Molecular Mechanics (MM2) Parameters for the (η3-Allyl)palladium Moiety," *J. Am. Chem. Soc.* 115(11):4859-4867 (abstract only).

Pregosin et al. (1994), "Selective Restricted Phenyl Rotation in an η3-Ph2C-CH-CHPh Allyl Sparteine Complex of Pd(II). Variable-Temperature 13C and Multinuclear Exchange Spectroscopy," *Magn. Reson. Chem.* 32(5):297-302 (abstract only).

Rush et al. (1997), "Palladium(II)-Catalyzed Olefin Addition Polymerizations of 3,3-Dialkyl-Substituted Cyclopropenes," *Macromolecules* 30(24):7375-7385 (abstract only).

* cited by examiner

METHODS AND COMPOSITIONS FOR ENANTIOSELECTIVE OXIDATION REACTIONS

CROSS REFERENCE TO RELATED APPLICATIONS

This application claims the benefit of U.S. Provisional Application Ser. No. 60/274,642 filed Mar. 12, 2001.

FIELD OF THE INVENTION

This invention relates to a method of catalyzing enantioselective oxidation reactions, including cyclization reactions, and a catalyst system for use in such reactions. More particularly, the invention relates to the enantioselective oxidation of an organic compound with a catalyst system to produce an oxidized organic compound and a single enantiomer of the organic compound. The invention finds utility in the resolution of enantiomers as well as in the selective production of compounds useful in organic synthesis methods, as either intermediates or final products, both of which possess commercial viability.

BACKGROUND OF THE INVENTION

Among the many hundred known processes for alcohol oxidation, comparatively few metal-catalyzed examples have been developed. One notable exception has been the use of catalytic palladium(II) systems, which often provide efficient oxidation of sec-alcohols to ketones in high yield (Blackburn et al., *J. Chem. Soc., Chem. Commun.* 157 (1977); Tamaru et al., *Tetrahedron Lett.* 20:1401 (1979); Nagashima et al., *Chem. Lett.* 1171 (1981); Aït-Mohand et al., *Tetrahedron Lett.* 36:2473 (1995); Peterson et al, *J. Org. Chem.* 63:3185 (1998); Nishimura et al., *J. Org. Chem.* 64:6750 (1999); and ten Brink et al., *Science* 287:1636 (2000)). Interestingly, palladium(II) oxidations have been successfully implemented using a wide variety of co-oxidants, including allyl carbonates, aryl halides, $CCl_4$, and molecular oxygen. The kinetic resolution of sec-alcohols has been studied in a number of systems that utilize chiral ligands. The exploratory studies that focused on chiral phosphine ligands in the presence of organic oxidants established that modest levels of asymmetric induction were attainable under a range of conditions. However, these studies also showed that reactions carried out under these conditions were plagued by a variety of side reactions and inconsistencies.

Therefore, the oxidation of secondary alcohols is one of the most common and well-studied reactions in chemistry. Although excellent catalytic enantioselective methods exist for a variety of oxidation processes, such as epoxidation, dihydroxylation, and aziridination, it is surprising that there are relatively few catalytic enantioselective examples of the ubiquitous alcohol oxidation.

Accordingly, there is a continuing need in the art for improved enantioselective oxidation methods, as well as improved methods of selectively oxidizing one isomer of a racemic mixture of compounds. Additionally, there is a need in the art for catalyst systems that are useful in such methods. The present invention addresses those needs.

SUMMARY OF THE INVENTION

One aspect of the invention relates to a method of catalyzing an enantioselective oxidation reaction of an organic compound, comprising: a) contacting the organic compound with i) an oxidizing agent, and ii) a catalyst comprising a metal composition and a chiral ligand, wherein the metal is selected from the group consisting of Group 8, Group 9 and Group 10 of the Periodic Table of the Elements; and b) producing an oxidized organic compound and a single enantiomer of the organic compound.

Another aspect of the invention pertains to a method of catalyzing an enantioselective oxidative cyclization reaction of an organic compound, comprising: a) contacting the organic compound with: i) an oxidizing agent, and ii) a catalyst comprising a metal composition and a chiral ligand, wherein the metal is selected from the group consisting of Group 8, Group 9 and Group 10 of the Periodic Table of the Elements; and b) producing a cyclic organic compound.

Yet another aspect of the invention relates to a catalyst system comprising: a) a metal composition, wherein the metal is selected from the group consisting of Group 8, Group 9 and Group 10 of the Periodic Table of the Elements; and b) a chiral ligand comprising: i) at least one chiral atom, and ii) two or more tertiary amines that are separated by two or more linking atoms.

Still another aspect of the invention relates to a catalyst system comprising: a) a chiral ligand having the structure:

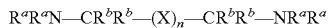

wherein each $R^a$ group is independently selected from the group consisting of alkyl, cycloalkyl, cycloheteroalkyl, aryl, heteroaryl and silyl; X is —$CR^bR^b$— or a heteroatom; n is an integer from 0–2; and each $R^b$ group is independently selected from the group consisting of hydrogen, alkyl, cycloalkyl, cycloheteroalkyl, aryl, heteroaryl and silyl; and wherein two or more of the $R^a$ and $R^b$ groups, together with the atoms to which they are attached, can be taken together to form one or more cyclic structures; complexed with b) a metal composition, wherein the metal is selected from the group consisting of Group 8, Group 9 and Group 10 of the Periodic Table of the Elements.

Still another aspect of the invention relates to a catalyst system comprising: a) a chiral ligand having the structure:

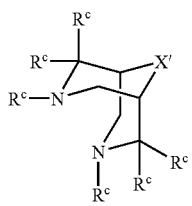

wherein each $R^c$ group is independently selected from the group consisting of alkyl, cycloalkyl, cycloheteroalkyl, aryl, heteroaryl and silyl; X' is selected from the group consisting of —O—, —S—, —$N(R^d)$—, —$C(R^d)_2$—, —C(O)—, —$C(NR^d)$—, —$C(OR^d)_2$—, and —$C(SR^d)_2$—; and each $R^d$ group is independently selected from the group consisting of hydrogen, alkyl, cycloalkyl, cyclobeteroalkyl, aryl, heteroaryl and silyl; and wherein two or more of the $R^c$ and $R^d$ groups, together with the atoms to which they are attached, can be taken together to form one or more cyclic structures; complexed with b) a metal composition, wherein the metal is selected from the group consisting of Group 8, Group 9 and Group 10 of the Periodic Table of the Elements.

DETAILED DESCRIPTION OF THE INVENTION

The present invention relates to methods and catalyst systems for catalyzing enantioselective oxidation reactions, including enantioselective oxidation reactions of secondary alcohols and other similarly reactive organic substrates. The methods and catalyst systems described herein are particularly useful for kinetic resolution of racemic mixtures of enantiomers, for example secondary alcohols. As will be described in detail below, the invention can provide a single enantiomer at an enantiomeric excess of greater than 99% from a racemic mixture of enantiomers, e.g., secondary alcohols.

Before describing detailed embodiments of the invention, it will be useful to set forth definitions that are used in describing the invention. The definitions set forth apply only to the terms as they are used in this patent and may not be applicable to the same terms as used elsewhere, for example in scientific literature or other patents or applications including other applications by these inventors or assigned to common owners. The following description of the preferred embodiments and examples are provided by way of explanation and illustration. As such, they are not to be viewed as limiting the scope of the invention as defined by the claims. Additionally, when examples are given, they are intended to be exemplary only and not to be restrictive. For example, when an example is said to "include" a specific feature, that is intended to imply that it may have that feature but not that such examples are limited to those that include that feature.

It must be noted that, as used in the specification and the appended claims, the singular forms "a," "an" and "the" include plural referents unless the context clearly dictates otherwise. Thus, for example, reference to "a compound" encompasses a combination or mixture of different compounds as well as a single compound, reference to "suitable solvent" includes a single such solvent as well as a combination or mixture of different solvents, and the like.

In describing and claiming the present invention, the following terminology will be used in accordance with the definitions set out below.

As used herein, the term "alkyl" refers to a branched or unbranched saturated hydrocarbon group typically although not necessarily containing about 1–24 carbon atoms, unless indicated otherwise. Exemplary alkyl groups include methyl, ethyl, n-propyl, isopropyl, n-butyl, isobutyl, t-butyl, n-amyl, isoamyl, n-hexyl, n-heptyl, n-octyl, n-decyl, hexyloctyl, tetradecyl, hexadecyl, eicosyl, tetracosyl, and the like, as well as cycloalkyl groups such as cyclopropyl, cyclobutyl, cyclopentyl, cyclohexyl, cycloheptyl, cyclooctyl and the like. Generally, although again not necessarily, alkyl groups herein contain about 1–12 carbon atoms. The term "lower alkyl" refers to an alkyl group of 1–6 carbon atoms, preferably 1–4 carbon atoms. The alkyl group is optionally substituted at one or more positions. Exemplary substituents include but are not limited to hydroxyl, cyano, alkoxy, =O, =S, —NO$_2$, halo, heteroalkyl, amine, thioether, —SH, and aryl. Accordingly, if not otherwise indicated, the terms "alkyl" includes branched, unbranched, unsubstituted, and substituted alkyl groups. The term "cycloalkyl" refers to a cyclic alkyl, as defined above, and is typically a stable 3- to 7 membered monocyclic or 7- to 10-membered polycyclic ring which is saturated or partially unsaturated (e. g., containing one or more double bonds). Similarly, the term "cycloheteroalkyl" is intended to mean a cyclic alkyl group, as defined above, that contains one or more heteroatoms, and is typically a stable 3- to 7 membered monocyclic or 7- to 10-membered polycyclic ring which is saturated or partially unsaturated and contains 1–4 heteroatoms (N, O, S, P or Si). As with alkyl, the terms "cycloalkyl" and "cycloheteroalkyl" are intended to include both unsubstituted and substituted groups. The substitutions can be on a carbon or a heteroatom if the resulting compound is stable. For example, any amino group contained within the heterocycloalkyl group can be a primary, secondary or tertiary amine, as long as the structure is stable.

As used herein, the term "aryl" is intended to mean an aromatic substituent containing a single aromatic ring (e.g., phenyl) or multiple aromatic rings that are fused together (e.g., naphthyl or biphenyl), directly linked, or indirectly linked (such that the different aromatic rings are bound to a common group such as a methylene or ethylene moiety). Typically, the aryl group comprises from 5–14 carbon atoms. Preferred aryl groups contain one aromatic ring or two fused or linked aromatic rings, e.g., phenyl, naphthyl, biphenyl, diphenylether, diphenylamine, benzophenone, and the like. The aryl moiety may be independently substituted with one or more substituent groups, typically 1–3 substituents, including =O, —OH, —COOH, —CH$_2$—SO$_2$-phenyl, —C$_{1-6}$alkyl, —O—C$_{1-6}$alkyl, —C(O)—C$_{1-4}$alkyl, —(CH$_2$)$_{0-2}$—C(O)—O—C$_{1-4}$alkyl, cycloalkyl, —C$_{1-6}$ alkoxy, halo, nitro, amino, alkylamino, dialkylamino, —C(O)—N(C$_{1-4}$alkyl)$_2$, —NH—C(O)—C$_{1-4}$alkyl, —C(O)—NH$_2$, —SO$_2$—NH$_2$, trifluoromethyl, cyano, aryl, benzyl, —O-aryl and —S-aryl. Thus, the term "aryl" includes unsubstituted and substituted aryl groups. The term "heteroaryl" refer to aryl, as defined above, in which at least one carbon atom, typically 1-3 carbon atoms, is replaced with a heteroatom N, O, S, P or Si). The heteroaryl can have the heteroatoms within a single ring, (e.g., such as pyridyl, imidazolyl, thiazolyl, pyrimidine, oxazolyl, and the like), or within two rings (e.g., indolyl, quinolinyl, benzofuranyl, and the like). As with aryl, the term "heteroaryl" is intended to include both unsubstituted and substituted heteroaryl groups. The substitutions can be on a carbon or a heteroatom if the resulting compound is stable. For example, any amino group contained within the heteroaryl group can be a primary, secondary or tertiary amine, as long as the structure is stable.

As used herein, the term "chiral ligand" is intended to mean any ligand known in the art that contains (a) at least one chiral atom and (b) two or more tertiary amines that are separated by two or more linking atoms. A chiral ligand can exist as two enantiomers of opposite configuration. One of skill in the art will appreciate that for any given asymmetric reaction, each enantiomer will produce products of opposite configuration from the other, but with the same conversion and optical purity. For purposes of illustration, the chiral ligand and product structures are shown herein for one enantiomer. It is understood, however, that the invention also pertains to the corresponding enantiomer(s) of opposite configuration. It is further understood that one of skill in the art can readily select the appropriate enantiomer to achieve the desired product configuration.

The term "chiral catalyst" is intended to mean a catalyst comprising a metal composition and a chiral ligand, wherein the metal is selected from the group consisting of Group 8, Group 9 and Group 10 of the Periodic Table of the Elements.

The term "cyclic structure" is intended to include cycloalkyl, cycloheteroalkyl, aryl and heteroaryl groups, as well as fused ring systems.

As used herein, the term "enantioselective oxidation" is intended to mean that the reaction either selectively oxidizes one isomer of a compound contained in a racemic mixture of the compound, or produces a compound as a single enantiomer from an achiral starting material.

The terms "enantiomeric excess" and "ee" are intended to represent the percentage of one enantiomer in a mixture of enantiomers. For example, the enantiomeric excess of an R-enantiomer in a mixture of R- and S-enantiomers can be determined by subtracting the amount of the S-enantiomer from the R-enantiomer, and dividing by the sum of the amount of R-enantiomer and S-enantiomer.

The term "heteroatom" refers to nitrogen, oxygen, sulfur, phosphorus and silicon. As a linker, the heteroatom is represented by —O—, —S—, —NR—, etc. The heteroatoms can exist in any of their chemically allowed oxidation states. Thus a sulfur heteroatom can be in the form of a sulfide, sulfoxide, or sulfone.

As used herein, the term "silyl" is intended to mean a silyl group (—SiH$_3$) or derivative thereof. The term silyl can thus be represented by the formula —SiR$_3$, where each R group is independently H, alkyl, cycloalkyl, cycloheteroalkyl, aryl or heteroaryl.

As used herein, the term "tertiary amine" is intended to mean a group of the formula R'—N(R")(R'''), where R', R", and R''' are the same or different moieties and are not hydrogen.

In describing and claiming the present invention, the following abbreviations will be used in accordance with the definitions set out below.

| ABBREVIATIONS | |
| --- | --- |
| allyl | —CH$_2$CHCH$_2$ |
| Ar | aryl |
| dba | dibenzylideneacetone |
| EtOAc | Ethyl acetate |
| Me | methyl |
| nbd | norbornadiene |
| Ac | Acetyl |
| Ph | phenyl |
| TLC | Thin-layer chromatography |

The invention provides for a method of catalyzing an enantioselective oxidation reaction of an organic compound, comprising: a) contacting the organic compound with i) an oxidizing agent, and ii) a catalyst comprising a metal composition and a chiral ligand, wherein the metal is selected from the group consisting of Group 8, Group 9 and Group 10 of the Periodic Table of the Elements; and b) producing an oxidized organic compound and a single enantiomer of the organic compound. Typically, the organic compound will be an alcohol, thiol, amine or phosphine.

In another embodiment of the invention the enantioselective oxidation reaction is a cyclization reaction of an organic compound. Typically, the organic compound will contain an olefin tethered to a nucleophilic atom, which can be carbon or a heteroatom.

By selectively oxidizing a single enantiomer according to the method of the invention, at least two products will be produced: the oxidized compound and the single enantiomer of the excess unreacted compound. In this reaction, a single enantiomer preferably is at least about 50%, more preferably greater than 60% and most preferably greater than 90% of the unreacted compound.

The oxidized organic compound may then be reduced back to its original state and oxidized again with the catalyst system of the invention to produce additional amounts of the single enantiomer and oxidized organic compound.

The oxidizing agent is preferably used in a stoichiometric amount.

Suitable oxidizing agents are those that effectively oxidize the organic compound without producing undesired by-products. In addition, it is preferred to use the oxidizing agent in a stoichiometric amount. Exemplary oxidants include, by way of illustration and not limitation, molecular oxygen, benzoquinone, Cu (I) salts, and Cu (II) salts. Molecular oxygen is particularly well suited for use in the methods of the invention.

The organic compound may be oxidized by contacting the organic compound with a catalyst system in a suitable organic solvent such as toluene, tert-amyl alcohol, CHCl$_3$, methylene chloride, 1,2-dichloroethane, and benzene. Other suitable solvents for oxidation reactions are well known in the art.

The catalyst system of the invention is a chiral catalyst comprising a Group 8, Group 9 or Group 10 metal and a chiral ligand, preferably an enantiomerically enriched chiral ligand. One embodiment of the invention relates to a catalyst system comprising: a) a metal composition, wherein the metal is selected from the group consisting of Group 8, Group 9 and Group 10 of the Periodic Table of the Elements; and b) a chiral ligand comprising: i) at least one chiral atom, and ii) two or more tertiary amines that are separated by two or more linking atoms. The catalyst systems finds particular use in enantioselective reactions, including but not limited to the enantioselective oxidation and oxidative cyclization reactions described herein.

The metal composition can comprise the metal itself or a source of the metal. Any metal from Group 8 (iron, ruthenium, osmium), Group 9 (cobalt, rhodium, iridium) or Group 10 (nickel, palladium, and platinum) of the Periodic Table of the Elements may be used in the catalyst system. Preferably, the metal is a Group 10 metal, more preferably palladium. Exemplary sources of metals include complexes, such as palladium (II) complexes. Exemplary palladium (II) complexes include, by way of illustration and not limitation, acetates such as Pd(OAc)$_2$ and other esters; Pd$_2$(dba)$_3$; [(allyl)PdCl]$_2$; halide complexes such as PdCl$_2$, and halide complexes with additional substituents such as Pd(CH$_3$CN$_2$)Cl$_2$, Pd(OCOCF$_3$), Pd(PhCN$_2$)Cl$_2$, PdCl$_2$ (cyclooctadiene) and Pd(nbd)Cl$_2$.

Another embodiment of the invention relates to a catalyst system comprising: a) a chiral ligand having the structure:

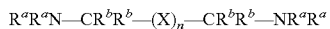

wherein each R$^a$ group is independently selected from the group consisting of alkyl, cycloalkyl, cycloheteroalkyl, aryl, heteroaryl and silyl; X is —CR$^b$R$^b$— or a heteroatom; n is an integer from 0–2; and each R$^b$ group is independently selected from the group consisting of hydrogen, alkyl, cycloalkyl, cycloheteroalkyl, aryl, heteroaryl and silyl; and wherein two or more of the R$^a$ and R$^b$ groups, together with the atoms to which they are attached, can be taken together to form one or more cyclic structures; complexed with b) a metal composition, wherein the metal is selected from the group consisting of Group 8, Group 9 and Group 10 of the Periodic Table of the Elements.

The catalyst systems finds particular use in enantioselective reactions, including but not limited to the enantioselective oxidation and oxidative cyclization reactions described herein.

In one preferred embodiment, n is 1.

Exemplary chiral ligands are set forth below:

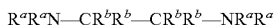

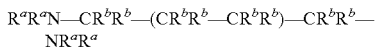

In another preferred embodiment of the chiral ligand, n is 1 and two or more of the $R^a$ and $R^b$ groups, together with the atoms to which they are attached, are taken together to form a four-ring structure. One such preferred four-ring structure is (−)-sparteine.

In another embodiment of the invention, the catalyst system comprises: a) a chiral ligand having the structure:

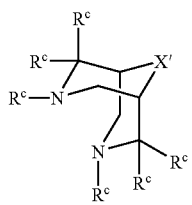

wherein each $R^c$ group is independently selected from the group consisting of alkyl, cycloalkyl, cycloheteroalkyl, aryl, heteroaryl and silyl; X' is selected from the group consisting of —O—, —S—, —N($R^d$)—, —C($R^d$)$_2$—, —C(O)—, —C(N$R^d$)—, —C(O$R^d$)$_2$—, and —C(S$R^d$)$_2$—; and each $R^d$ group is independently selected from the group consisting of hydrogen, alkyl, cycloalkyl, cycloheteroalkyl, aryl, heteroaryl and silyl; and wherein two or more of the $R^c$ and $R^d$ groups, together with the atoms to which they are attached, can be taken together to form one or more cyclic structures; complexed with b) a metal composition, wherein the metal is selected from the group consisting of Group 8, Group 9 and Group 10 of the Periodic Table of the Elements.

In one preferred embodiment, X' is —C$R^d R^d$ and two or more of the $R^c$ and $R^d$ groups, together with the atoms to which they are attached, are taken together to form a four-ring structure. One such structure of the chiral ligand is (−)-sparteine.

As noted above, the invention provides for a method of catalyzing an enantioselective oxidation reaction of an organic compound, comprising: a) contacting the organic compound with i) an oxidizing agent, and ii) a catalyst comprising a metal composition and a chiral ligand, wherein the metal is selected from the group consisting of Group 8, Group 9 and Group 10 of the Periodic Table of the Elements; and b) producing an oxidized organic compound and a single enantiomer of the organic compound. This method finds utility in several enantioselective oxidation reactions.

Performing enantioselective oxidation reactions with the chiral catalyst of the invention has the added advantage that only one oxidant is needed. Most oxidation reactions that utilize a Group 8, 9 or 10 metal catalyst include a co-oxidant to reoxidize the metal. In the methods of the invention, the oxidant (e.g., molecular oxygen) also serves as the co-oxidant.

Kinetic Resolution of Racemic Mixtures

In one embodiment of the invention, the enantioselective oxidation reaction is the kinetic resolution of a racemic mixture to provide an enantioenriched product. Scheme I illustrates one such reaction, where the kinetic resolution of the racemic mixture (±)-I.1 provides the enantioenriched product I.1. It is understood however, that other compounds that undergo this type of reaction can be used instead of compound (±)-I.1.

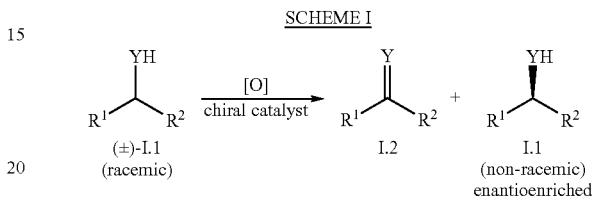

where $R^1$ and $R^2$ are independently selected from the group consisting of alkyl, cycloalkyl, cycloheteroalkyl, aryl, heteroaryl, silyl and substituted vinyl, or $R^1$ and $R^2$ are taken together to form a cycloalkyl; Y is selected from the group consisting of O, N$R^3$, S and P$R^3$; and $R^3$ is selected from the group consisting of H, alkyl, cycloalkyl, cycloheteroalkyl, aryl, heteroaryl, silyl and substituted vinyl.

A variation on this resolution reaction is shown in Scheme II:

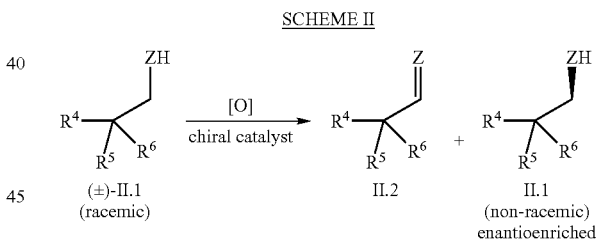

where $R^4$, $R^5$ and $R^6$ are independently selected from the group consisting of alkyl, cycloalkyl, cycloheteroalkyl, aryl, heteroaryl, silyl and substituted vinyl; Z is selected from the group consisting of O, N$R^7$, S and P$R^7$; and $R^7$ is selected from the group consisting of H, H, alkyl, cycloalkyl, cycloheteroalkyl, aryl, heteroaryl, silyl and substituted vinyl.

In one embodiment of the invention, the racemic mixture in Scheme I is an alcohol (Y=O). The alcohol preferably has an oxidizable, secondary functional group, for example a chiral secondary alcohol. The method and catalyst system of the invention can be used to achieve enantiomeric excesses of the unreacted alcohol of greater than 90%. The selective oxidation of a secondary alcohol is readily accomplished using molecular oxygen as the terminal oxidant, as shown in Scheme I. A preferred solvent is toluene. An exemplary reaction is shown in Scheme Ia:

SCHEME Ia

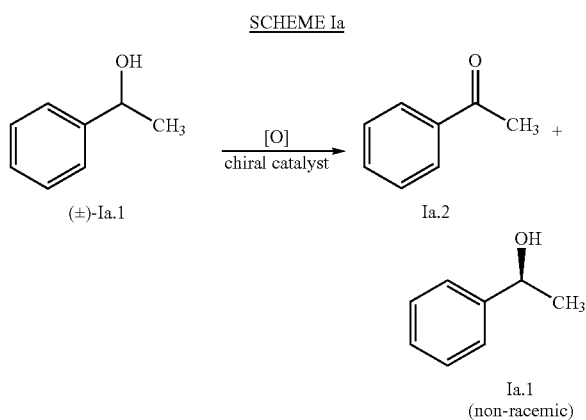

Enantioselective Wacker-type Cyclization

The oxidation of ethylene to acetaldehyde, commonly referred to as the Wacker oxidation reaction (Smidt et al., *Angew. Chem.* 71:176 (1959); Smidt et al., *Angew. Chem., Int. Ed Engl.* 1:80 (19620; and Smidt, *J. Chem. Ind.* 54 (1962)), is one of the best-known reactions catalyzed by palladium(II). Typically, palladium is complexed with a copper co-oxidant to re-oxidize the palladium, such as $PdCl_2$—$CuCl_2$. This oxidation reaction is useful in the synthetic transformation of olefins, but there has been minimal work on catalyzed enantioselective Wacker-type cyclization reactions. See for example, Uozumi et al., *J. Org. Chem.* 63:5071–5075 (1998), where a Pd-borax catalyst was used in combination with benzoquinone as the co-oxidant.

Accordingly, in one embodiment of the invention, the enantioselective oxidation reaction is an enantioselective Wacker-type cyclization reaction. Scheme III illustrates one such reaction. It is understood however, that other compounds that undergo this type of reaction can be used instead of compound III.1. For example, the compound can have one or more substitutions on the aromatic ring or the compound may be a cycloalkyl, cycloheteroalkyl, heteroaryl or other aryl ring.

Scheme III

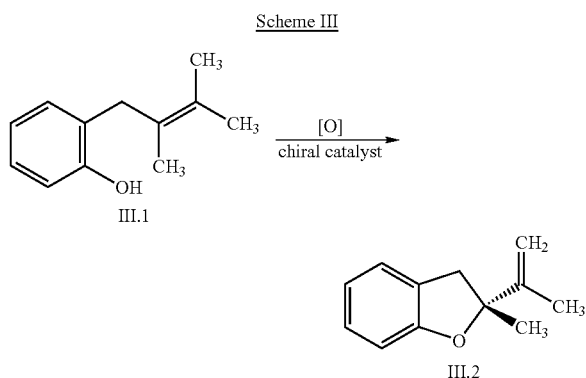

Performing an enantioselective Wacker-type cyclization reaction with the chiral catalyst of the invention has the added advantage that the reaction can be conducted in the absence of a co-oxidant, i.e., only one oxidant is needed, as compared to state of the art reactions that require a co-oxidant such as benzoquinone or a cupric chloride.

Enantioselective Aromatic Oxidation

In one embodiment of the invention, the enantioselective oxidation reaction is an enantioselective aromatic oxidation reaction. This reaction typically involves the oxidation of a hydroxymethylphenol to a spiro epoxy cyclohexadienone. Scheme IV illustrates one such reaction. It is understood however, that other compounds that undergo this type of reaction can be used instead of compound IV.1. For example, the compound can have one or more substitutions on the aromatic ring or the compound may be a heteroaryl or other aryl ring.

SCHEME IV

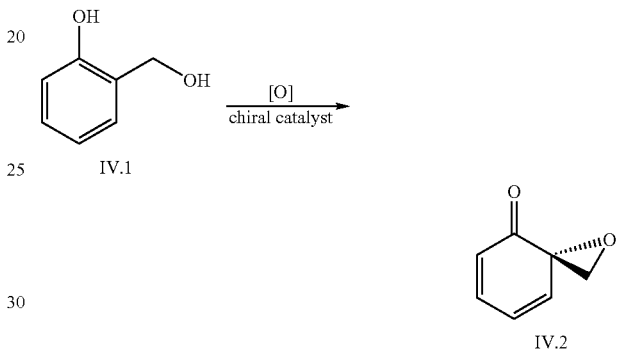

Enantio-group Differentiation of Meso Diols

In one embodiment of the invention, the enantioselective oxidation reaction is the enantio-group differentiation of meso diols. Scheme V illustrates one such reaction. It is understood however, that other meso diol compounds that undergo this type of reaction can be used instead of compound V.1. For example, there can be one or more substitutions on the cycloalkyl ring or the compound may be a cycloheteroalkyl, heteroaryl, aryl or other cycloalkyl ring. In addition, the hydroxyl groups can be part of a cyclic ring.

SCHEME V

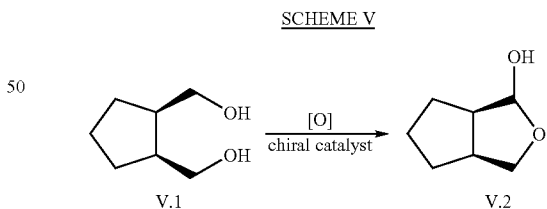

Another example of an enantio-group differentiation of meso diols is described in Example 3.

Enantioselective Oxidative [4+2] Cycloadditions

In one embodiment of the invention, the enantioselective oxidation reaction is an enantioselective oxidative [4+2] cycloaddition reaction. Scheme VI illustrates one such reaction. It is understood however, that other compounds that undergo this type of reaction can be used instead of compound VI.1.

SCHEME VI

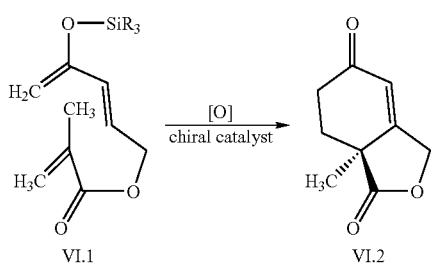

where —SiR$_3$ is a silyl group or derivative thereof, as defined above.

C—C Bond Forming Cyclization

In one embodiment of the invention, the enantioselective oxidation reaction is a C—C bond forming cyclization reaction. Scheme VII illustrates one such reaction. It is understood however, that other compounds that undergo this type of reaction can be used instead of compound VII.1.

SCHEME VII

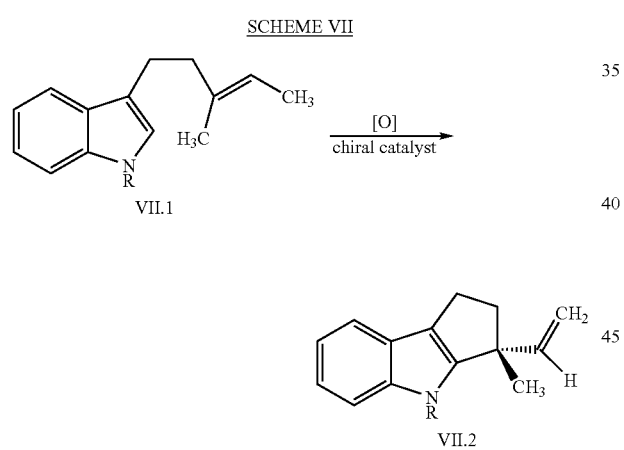

where R is selected from the group consisting of H, alkyl, cycloalkyl, cycloheteroalkyl, aryl and heteroaryl.

Enantioselective Oxidative Cyclization Reactions

As noted above, the invention also provides for a method of catalyzing an enatioselective oxidative cyclization of an organic compound. Exemplary cyclization reactions, as shown in Schemes VIII, IX and X. It is understood however, that other compounds that undergo these types of reactions can be used instead of compounds VIII.1, IX.1 and X.1. For example, the carbon atoms in these compounds can have one or more substituents (e.g., alkyl, cycloalkyl, cycloheteroalkyl, aryl and heteroaryl groups).

SCHEME VIII

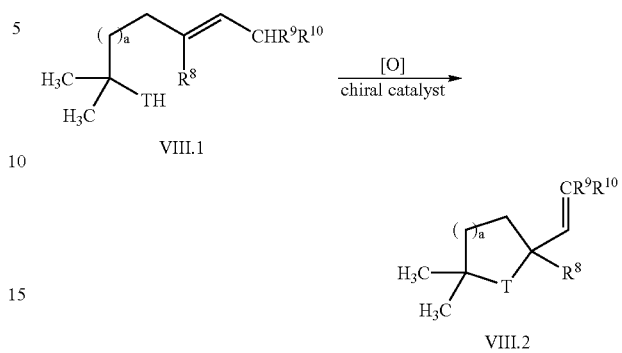

wherein $R^8$, $R^9$ and $R^{10}$ are independently selected from the group consisting of H, alkyl, cycloalkyl, cycloheteroalkyl, aryl, heteroaryl, silyl and substituted vinyl; T is selected from the group consisting of O, $NR^{11}$, S and $PR^{11}$; $R^{11}$ is selected from the group consisting of H, alkyl, cycloalkyl, cycloheteroalkyl, aryl, heteroaryl, silyl and substituted vinyl; and a is an integer from 1 to 3.

SCHEME IX

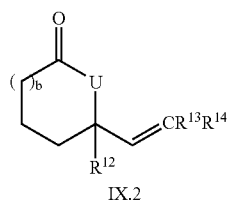

wherein $R^{12}$, $R^{13}$ and $R^{14}$ are independently selected from the group consisting of H, alkyl, cycloalkyl, cycloheteroalkyl, aryl, heteroaryl, silyl and substituted vinyl; T is selected from the group consisting of O, $NR^{15}$, S and $PR^{15}$; $R^{15}$ is selected from the group consisting of H, alkyl, cycloalkyl, cycloheteroalkyl, aryl, heteroaryl, silyl and substituted vinyl; and b is an integer from 0 to 2.

SCHEME X

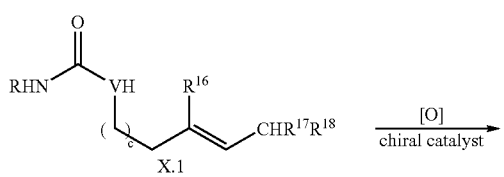

-continued

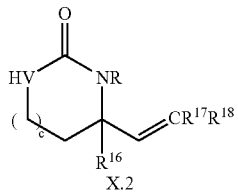

wherein $R^{16}$, $R^{17}$ and $R^{18}$ are independently selected from the group consisting of H, alkyl, cycloalkyl, cycloheteroalkyl, aryl, heteroaryl, silyl and substituted vinyl; T is selected from the group consisting of O, $NR^{19}$, S and $PR^{19}$; $R^{19}$ is selected from the group consisting of H, alkyl, cycloalkyl, cycloheteroalkyl, aryl, heteroaryl, silyl and substituted vinyl; and c is an integer from 0 to 2.

In addition to the reactions illustrated above as Schemes I–X, the catalyst system of the invention finds utility in the improved synthesis of numerous pharmaceutical agents that have chiral centers. Such pharmaceutical agents can thus exist as a mixture of enantiomers. When chemically synthesized, the resulting product is often a racemic mixture in which typically only one enantiomer is optically active. Thus, the product must be resolved prior to use. This additional step is often lengthy and can involve loss of up to half of the material. Thus if these pharmaceutical agents could be synthesized by an enantioselective reaction, only the optically active enantiomer would be produced.

The following list of pharmaceutical agents and reaction steps is intended to be merely illustrative and not limiting in scope.

The traditional synthesis of pharmaceutical agents such as amosulalol, bamethan, bitolterol, denopamine, fluoxetine and isoprenaline, involves a reduction step using a Pd—C catalyst. The traditional synthesis of pharmaceutical agents such as epinephrine, etilefrine and mefruside, involves a reduction step using a Raney-Ni catalyst. The traditional synthesis of pharmaceutical agents such as mefloquine, involves a reduction step using a Pt catalyst. The traditional synthesis of pharmaceutical agents such as metaraminol, involves an reductive amination step using a Pd—C catalyst. The catalyst system of the invention can be used in combination with any of the aforementioned catalysts to achieve a kinetic resolution of the alcohol, resulting in an enantiopure chiral drug.

The traditional synthesis of pharmaceutical agents such as clorprenaline, eprozinol, fexofenadine hydrochloride, isoconazole, mabuterol and miconazole, involves a reduction step using $NaBH_4$. The catalyst system of the invention can be used in combination with $NaBH_4$ to achieve a kinetic resolution of the alcohol, resulting in an enantiopure chiral drug.

The catalyst system of the invention also finds utility in the synthesis of pharmaceutical agents such as bromazine, carbocisteine, chloramphenicol, econazole, fadrozole, fenipentol, fenticonazole, fexofenadine, fluoxitine, mefloquine, montelukast sodium, and cloperastine, whose traditional synthesis involves a step using a racemic benzylic alcohol starting material, which could undergo oxidative kinetic resolution to provide enantiopure starting materials and thus an enantiopure chiral drug.

The catalyst system of the invention also finds utility in the synthesis of pharmaceutical agents such as chlorcyclizine, clobenztropine, whose traditional synthesis involves a step using a racemic benzylic chloride starting material, which could be alternatively prepared from the corresponding alcohol. Thus, oxidative kinetic resolution of the benzylic alcohol would provide enantiopure starting materials and thus an enantiopure chiral drug.

EXAMPLES

The practice of the present invention will employ, unless otherwise indicated, conventional techniques of pharmaceutical formulation, medicinal chemistry, and the like, which are within the skill of the art. Such techniques are explained fully in the literature. Preparation of various types of pharmaceutical formulations are described, for example, in *Remington: The Science and Practice of Pharmacy*, Nineteenth Edition. (1995) cited supra and Ansel et al., *Pharmaceutical Dosage Forms and Drug Delivery Systems*, 6th Ed. (Media, PA: Williams & Wilkins, 1995).

The following examples are put forth so as to provide those of ordinary skill in the art with a complete disclosure and description of how to make and use the compounds of the invention, and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric. All components were obtained commercially unless otherwise indicated.

Materials and Methods

Unless stated otherwise, reactions were performed in flame-dried glassware under a nitrogen or an argon atmosphere, using freshly distilled solvents. All other commercially obtained reagents were used as received. Reaction temperatures were controlled by an IKAmag temperature modulator. TLC was performed using E. Merck silica gel 60 F254 precoated plates (0.25 mm). ICN Silica gel (particle size 0.032–0.063 mm) was used for flash chromatography. $^1H$ and $^{13}C$ NMR chemical shifts are reported relative to $Me_4Si$ (δ 0.0). Analytical chiral HPLC was performed on a Chiralcel OJ, AS, or OD-H column (each is 4.6 mm×25 cm) obtained from Daicel Chemical Industries, Ltd. Analytical achiral GC was performed using an Agilent DB-WAX (30.0 m×0.25 m) column. Analytical chiral GC was carried out using a Chiraldex B-DM column (30.0 m×0.25 mm) purchased from Bodman Industries. Commercially available racemic alcohols in Table 3 (entries 1, 2, 3, 5, 7, 8, and 9) were purchased from the Sigma-Aldrich Chemical Company (Milwaukee, Wis.). Non-commercially available racemic alcohols used in Table 3 (corresponding to entries 4, 6, and 10) were prepared as described in Ruble et al., *J. Am. Chem. Soc.* 119:1492 (1997) and Ruble et al., *J. Org. Chem.* 63:2794 (1998). Commercially available samples of enantiopure alcohols for analytical comparison purposes (entries 1, 4, 7, 8, and 9) were also purchased from the Sigma-Aldrich Chemical Company. Non-commercially available enantiopure alcohols were prepared by palladium-catalyzed oxidative kinetic resolution (Table 3 entries 2 [Nakamura et al *J. Chem. Soc., Perkin. Trans.* 1:2397.3 (1999)], 3 [Nieduzak et al., *Tetrahedron: Asymmetry* 2:113.4 (1991)], 5 [Bakker et al., *Tetrahedron: Asymmetry* 11:1801.5 (2000)], 6 [Nakamura et al., *J. Org. Chem.* 63:8957.6 (1998)] and 10 [Argus et al., *J. Chem. Soc.* 1195 (1960)]) were compared by optical rotation to known values.

Example 1

General Procedure for the Oxidative Kinetic Resolution of Secondary Alcohols Ligand and Palladium Source Screening Trials A 25 mL Schlenk flask equipped with a magnetic stir bar was charged with powdered molecular sieves (MS3 Å, 0.25 g) and flame-dried under vacuum. After cooling under dry $N_2$, Pd complex (0.025 mmol, 0.05 equiv) was added followed by toluene (5.0 mL), and an appropriate ligand (0.10 mmol, 0.20 equiv). For experiments which probed the effect of the chiral ligand, the appropriate ligand was used in the same general procedure with $Pd(OAc)_2$ (Reaction 1). For experiments that probed the effect of the palladium source, the appropriate Pd complex was used in the same general procedure (Reaction 2). The structures of all chiral ligands tested are provided below:

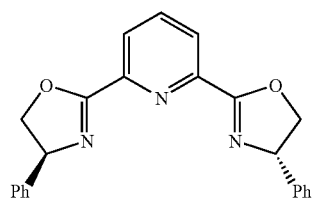

(S,S)-Ph-PYBOX

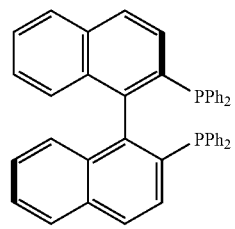

(R)-BINAP

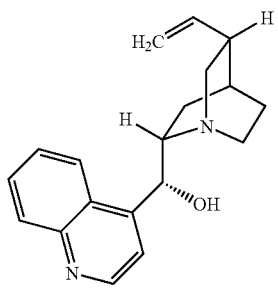

(−)-cinchonidine

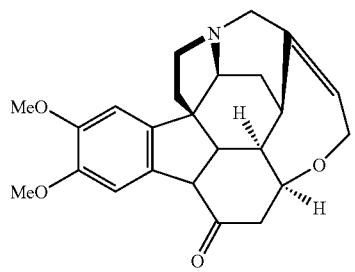

(−)-brucine

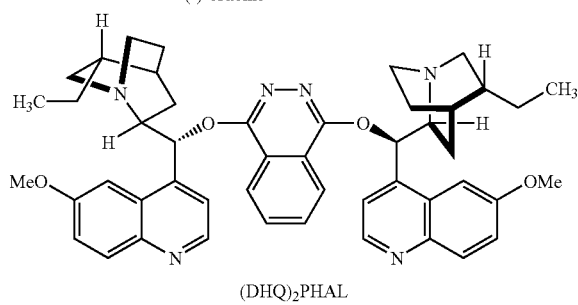

(DHQ)₂PHAL

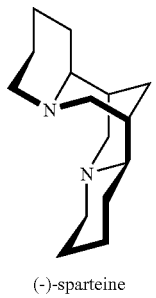

(−)-sparteine

Using 1-phenylethanol (±)-I1.1 as the alcohol, the conditions developed by Uemura (Nishimura et al., *J. Org. Chem.* 64:6750–6755 (1999)), incorporated herein by reference, were used to test a variety of chiral ligands. The flask was vacuum evacuated and filled with $O_2$ (3×, balloon), and the reaction mixture was heated to 80° C. for 10 min. The alcohol (±)-I1.1 (0.50 mmol, 1.0 equiv) was introduced and the reaction monitored by standard analytical techniques (TLC, GC, $^1$H-NMR, and HPLC) for % conversion and enantiomeric excess values. Aliquots of the reaction mixture (0.2 mL) were collected after 24 h, 40 h, 72 h, 96 h, 120 h, and 144 h depending on the course of the reaction (typically three aliquots per run). Each aliquot was filtered through a small plug of silica gel (EtOAc eluent), evaporated and analyzed. Percent conversions were measured by GC integration of the alcohol and the ketone peaks, correcting for response factors.

Reaction 1

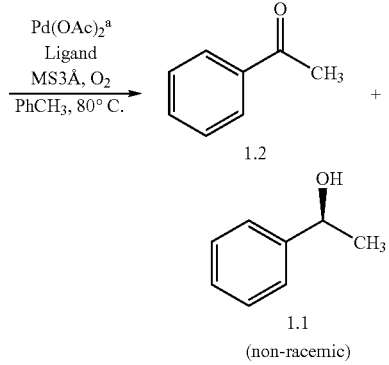

[a] 5 mol % Pd(OAc)₂, 20 mol % ligand, 1 atm O₂

After testing many structurally diverse ligands (shown above) in the oxidation reaction, (−)-sparteine emerged as a preferred ligand, as shown in Table 1:

TABLE 1

Ligand Screen for the Pd-Catalyzed Oxidative Kinetic Resolution of 1-Phenylethanol

| Entry | Ligand | Time | Conversion | ee ROH[a] | s[b] |
|---|---|---|---|---|---|
| 1 | (S,S)-Ph-PYBOX | 72 h | 2% | — | 1 |
| 2 | (R)-BINAP | 24 h | 29.0% | 0% | 1 |
| 3 | (−)-cinchonidine | 72 h | 2% | — | 1 |
| 4 | (−)-brucine | 24 h | 77.0% | 0% | 1 |

TABLE 1-continued

Ligand Screen for the Pd-Catalyzed
Oxidative Kinetic Resolution of 1-Phenylethanol

| Entry | Ligand | Time | Conversion | ee ROH[a] | s[b] |
|---|---|---|---|---|---|
| 5 | (DHQ)$_2$PHAL | 24 h | 31.6% | 8.7% | 1.6 |
| 6 | (−)-sparteine | 24 h | 15.1% | 13.7% | 8.8 |

[a] ee ROH = enantiomeric excess of alcohol
[b] s = selectivity

The nature of the palladium source was found to be critical (see Table 2 for conversion rates).

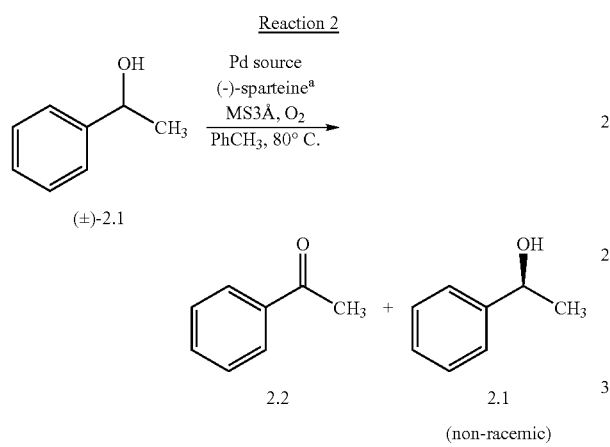

(non-racemic)

[a] 5 mol% Pd, 20 mol% (−)-sparteine, 1 atm O$_2$.

It was found that substituting PdCl$_2$ for Pd(OAc)$_2$ induced a marked increase in the selectivity factor(s). For example, oxidative kinetic resolution of 1-phenylethanol (±)-2.1 using Pd(OAc)$_2$ proceeded with a selectivity factor of 8.8, whereas the analogous resolution using PdCl$_2$ was found to have a selectivity factor of 16.3, thereby providing acetophenone in 62.6% conversion and unreacted alcohol of 98.0% ee. Further screening of the palladium source resulted in the discovery that Pd(nbd)Cl$_2$ provided an even more active catalytic system (Table 2, entry 7, s=23.1).

TABLE 2

Importance of the Palladium Source
for the Oxidative Kinetic Resolution of 1-Phenylethanol

| Entry | Pd source | Time | Conversion | ee ROH[a] | s[b] |
|---|---|---|---|---|---|
| 1 | Pd(OAc)$_2$ | 24 h | 15.1% | 13.7% | 8.8 |
| 2 | Pd$_2$(dba)$_3$ | 55 h | 66.2% | 81.5% | 5.7 |
| 3 | PdCl$_2$ | 96 h | 62.6% | 98.0% | 16.3 |
| 4 | Pd(CH$_3$CN)$_2$Cl$_2$ | 36 h | 51.7% | 79.8% | 16.5 |
| 5 | Pd(PhCN)$_2$Cl$_2$ | 36 h | 57.4% | 92.1% | 16.9 |
| 6 | [(allyl)PdCl]$_2$ | 96 h | 60.2% | 96.9% | 18.0 |
| 7 | Pd(nbd)Cl$_2$ | 96 h | 59.9% | 98.7% | 23.1 |

[a] ee ROH = enantiomeric excess of alcohol
[b] s = selectivity

General Procedure for the Oxidative Kinetic
Resolution of Secondary Alcohols Preparative Runs
(6.0 mmol in Table 3)

A 200 mL flask equipped with a magnetic stir bar was charged with powdered molecular sieves (MS3 Å, 3.0 g) and flame-dried under vacuum. After cooling under dry N$_2$, Pd(nbd)Cl$_2$ (80.8 mg, 0.30 mmol, 0.05 equiv) was added followed by toluene (60.0 mL), and (−)-sparteine (276 μL, 1.20 mmol, 0.20 equiv). The flask was vacuum evacuated and filled with O$_2$ (3×, balloon), and the reaction mixture was heated to 80° C. for 10 min. The racemic alcohol (6.00 mmol, 1.0 equiv) was introduced and the reaction monitored by standard analytical techniques (TLC, GC, $^1$H-NMR, and HPLC) for % conversion and enantiomeric excess values. Aliquots of the reaction mixture (0.2 mL) were collected after 24 h, 40 h, 72 h, 96 h, 120 h, and 144 h depending on the course of the reaction (typically three aliquots per run). Each aliquot was filtered through a small plug of silica gel (EtOAc eluent), evaporated and analyzed. Upon completion of the reaction, the reaction mixture was filtered through a pad of SiO$_2$ (EtOAc eluent) and purified by column chromatography on SiO$_2$.

General Procedure for the Oxidative Kinetic
Resolution of Secondary Alcohols Preparative Runs
(8.0 mmol in Table 3)

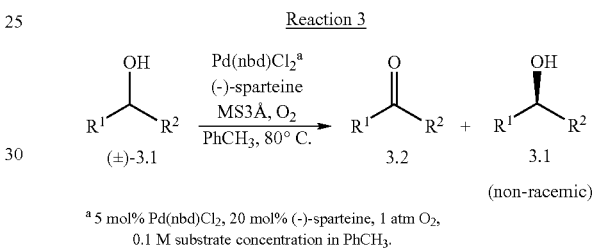

(non-racemic)

[a] 5 mol% Pd(nbd)Cl$_2$, 20 mol% (−)-sparteine, 1 atm O$_2$, 0.1 M substrate concentration in PhCH$_3$.

A 200 mL flask equipped with a magnetic stir bar was charged with powdered molecular sieves (MS3 Å, 4.0 g) and flame-dried under vacuum. After cooling under dry N$_2$, Pd(nbd)Cl$_2$ (108 mg, 0.40 mmol, 0.05 equiv) was added followed by toluene (80.0 mL), and (−)-sparteine (368 μL, 1.60 mmol, 0.20 equiv). The flask was vacuum evacuated and filled with O$_2$ (3×, balloon), and the reaction mixture was heated to 80° C. for 10 min. The alcohol (±)-3.1 (8.00 mmol, 1.0 equiv) was introduced and the reaction monitored by standard analytical techniques (TLC, GC, $^1$H-NMR, and HPLC) for % conversion and enantiomeric excess values. Aliquots of the reaction mixture (0.2 mL) were collected after 24 h, 40 h, 72 h, 96 h, 120 h, and 144 h depending on the course of the reaction (typically three aliquots per run). Each aliquot was filtered through a small plug of silica gel (EtOAc eluent), evaporated and analyzed. Upon completion of the reaction, the reaction mixture was filtered through a pad of SiO$_2$ (EtOAc eluent) and purified by column chromatography on SiO$_2$.

As shown in Table 3, palladium-catalyzed kinetic resolutions with (−)-sparteine as a ligand provide uniformly excellent levels of asymmetric induction with a variety of activated alcohols (i.e., benzylic and allylic). Benzylic alcohols with functionalized aromatic rings serve particularly well as substrates for oxidative kinetic resolution, with selectivity factors as high as 32 (entries 1–7). Additionally, the resolution is not limited to 1-substituted ethanol derivatives (entries 7–9). Substrates containing fused ring systems are also resolved to high levels of enantiopurity (entries 8 and 9, ee>93%). Importantly, the potential utility and versatility of the catalytic oxidative kinetic resolution is further established by the reaction of a substituted allylic alcohol (entry 10). In all cases, the absolute stereoconfiguration of the enantioenriched alcohol could be determined by comparison to data from known optically pure substance as was consistent with that shown in Table 3.

Data for the following racemic alcohols (±)-3.1 is shown Table 3:

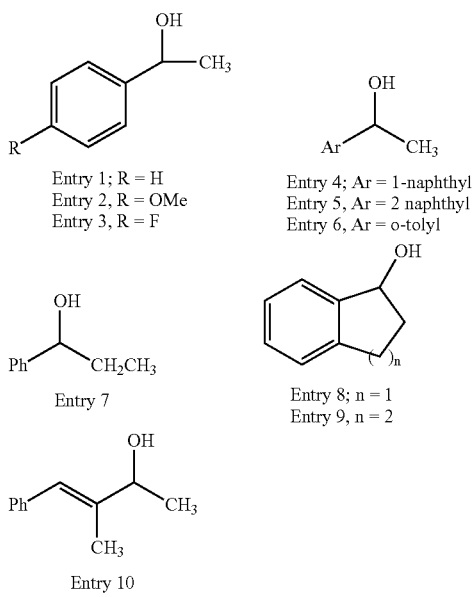

Data for the unreacted alcohols 3.1 (major enantiomers) is also presented in Table 3. The unreacted alcohols have the following structures, with the numbers corresponding to the equivalent racemic alcohol shown above:

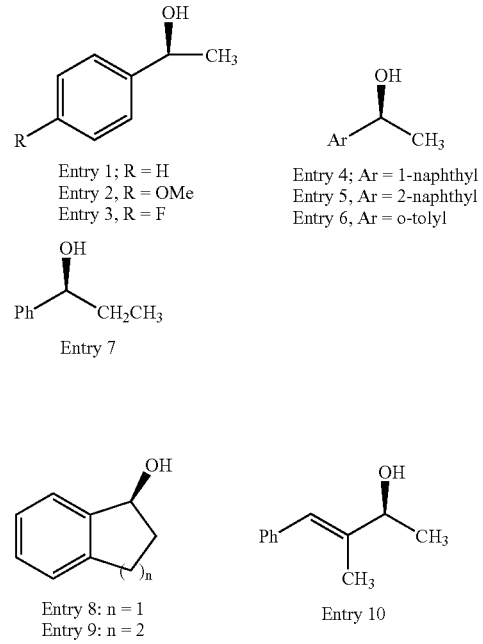

The chromatography eluent for Entries 1–6, 8 and 10 was 6:1→3:1 hexanes/EtOAc. The chromatography eluent for Entry 7 was 6:1→4:1 hexanes/EtOAc and the chromatography eluent Entry 9 was 9:1→4:1 hexanes/EtOAc.

TABLE 3

The Oxidative Kinetic Resolution of Secondary Alcohols

| Entry | Amount | Time | C | Isolated yield of ketone | Isolated yield ROH | ee ROH[b] | s[c,d] |
|---|---|---|---|---|---|---|---|
| 1 | 0.977 g (8.00 mmol) | 96 h | 59.9% | 0.535 g (56%) | 0.366 g (37%) | 98.7% | 23.1 |
| 2 | 1.22 g (8.00 mmol) | 96 h | 66.6% | 0.773 g (64%) | 0.392 g (32%) | 98.1% | 12.3 |
| 3 | 1.12 g (8.00 mmol) | 54 h | 63.3% | 0.623 g (56%) | 0.361 g (32%) | 97.4% | 14.4 |
| 4 | 1.03 g (6.00 mmol) | 192 h | 55.9% | 0.555 g (54%) | 0.443 g (43%) | 78.4% | 9.8 |
| 5 | 5.00 g (29.00 mmol) | 112 h | 55.2% | 2.75 g (55%) | 2.20 g (44%) | 99.0% | 47.1 |
| 6 | 1.09 g (8.00 mmol) | 144 h | 48.4% | 0.492 g (46%) | 0.533 g (49%) | 68.7% | 13.1 |
| 7 | 1.09 g (8.00 mmol) | 192 h | 59.3% | 0.625 g (58%) | 0.435 g (40%) | 93.1% | 14.8 |
| 8 | 1.07 g (8.00 mmol) | 54 h[e] | 67.5% | 0.662 g (63%) | 0.323 g (30%) | 93.4% | 8.3 |
| 9 | 1.19 g (8.00 mmol) | 40 h | 68.6% | 0.796 g (68%) | 0.370 g (31%) | 99.8% | 15.8 |
| 10 | 0.973 g (6.00 mmol) | 120 h | 70.4% | 0.671 g (70%) | 0.286 g (29%) | 91.8% | 6.6 |

[b] ee ROH = enantiomeric excess of alcohol. The degree of enantioselectivity was measured directly by chiral HPLC or GC of the recovered alcohols. Enantiomeric excess was measured by chiral HPLC analysis using either a Chiralcel OJ, AS or OD-H column or by chiral GC using a Bodman Chiraldex B-DM columns. Conversion ("C") was measured by GC using a DB-WAX column.
[c] s = selectivity. Selectivity values represent an average of at least two experiments, while conversion and ee values are for specific cases.
[d] For each entry, comparable selectivities are observed throughout the course of the run.
[e] Performed at 60° C.

Example 2

Scale-up Procedure for the Oxidative Kinetic Resolution of α-Methyl-2-Naphthalenemethanol (4.1): 1$^{st}$ Cycle Particularly noteworthy is the preparative reaction shown in Reaction 4. The oxidative kinetic resolution performed well on multigram scale with good recovery (44%) of optically enriched alcohol (−)-4.1 in 99% ee. Quantitative reduction of ketone 4.2 provides an opportunity for the preparation of chiral alcohol (−)-4.1 in >50% overall yield from a racemic mixture via multiple oxidative kinetic resolution cycles.

Regeneration of Alcohol ((±)-4.1)

A cooled (0° C.) solution of ketone 4.2 (2.75 g, 16.2 mmol, 1.0 equiv) in 1:1 CH$_2$Cl$_2$/MeOH (16.2 mL) was treated with NaBH$_4$ (733 mg, 19.4 mmol, 1.2 equiv) in four portions over 10 min. The reaction was stirred at 0° C. for 15 min, and treated with 1 N HCl solution (30 mL) slowly over 15 min. After the evolution of gas was complete, the layers were separated, and the aqueous layer extracted with CH$_2$Cl$_2$ (3×30 mL). The combined organic layers were dried over MgSO$_4$, evaporated, and purified by flash chromatography on silica gel (3:1 hexanes/EtOAc eluent) to provide alcohol (±)-4.1 (2.76 g, 99% yield) as a white solid, which was used in cycle two.

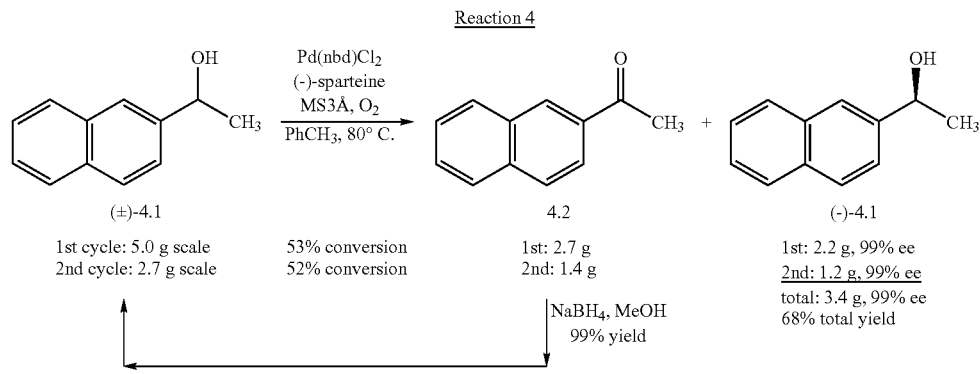

Reaction 4

A 500 mL round bottom flask was charged with powdered molecular sieves (MS3 Å, 14.5 g) and a magnetic stir bar and flame-dried under vacuum. After cooling under dry N$_2$, Pd(nbd)Cl$_2$ (0.391 g, 1.45 mmol, 0.05 equiv) was added followed by toluene (290 mL,), and (−)-sparteine (1.34 mL, 5.81 mmol, 0.20 equiv). The flask was vacuum evacuated and filled with O$_2$ (3×, balloon), and the reaction mixture was heated to 80° C. for 10 min. Alcohol (±)-4.1 (5.00 g, 29.0 mmol, 1.0 equiv) was introduced and the reaction mixture heated at 80° C. for 112 h. Progress of the reaction was monitored by standard analytical techniques (TLC, GC, $^1$H-NMR, and HPLC) for % conversion and enantiomeric excess values by the removal of small aliquots of the reaction mixture (0.2 mL) which were filtered through silica gel (EtOAc eluent), evaporated and analyzed. After the reaction rate had significantly slowed (112 h, 55% conversion), and aliquot analysis showed high levels of enantiocontrol for the remaining alcohol (−)-4.1 (99.0% ee), the entire reaction mixture was filtered through a small column of silica gel (5×6 cm, EtOAc eluent). The filtrate was evaporated and purified by flash chromatography on silica gel (6:1→3:1 hexanes/EtOAc eluent) to provide ketone 4.2 (R$_F$=0.56, 2.75 g, 55% yield) and alcohol (−)-4.1 (R$_F$=0.44, 2.20 g, 44% yield, 99.0% ee) as white solids.

2$^{nd}$ Cycle

A 500 mL round bottom flask was charged with Molecular Sieves (MS3 Å, 8.0 g) and flame-dried under vacuum. After cooling under dry N$_2$, Pd(nbd)Cl$_2$ (0.216 g, 0.800 mmol, 0.05 equiv) was added followed by toluene (160 mL), and (−)-sparteine (0.735 mL, 3.20 mmol, 0.20 equiv). The flask was vacuum evacuated and filled with O$_2$ (3×, balloon), and the reaction mixture was heated to 80° C. for 10 min. Alcohol (±)-4.1 (2.76 g, 16.0 mmol, 1.0 equiv) prepared above was introduced and the reaction mixture heated at 80° C. for 96 h. Progress of the reaction was monitored by standard analytical techniques (TLC, GC, $^1$H-NMR, and HPLC) for % conversion and enantiomeric excess values by the removal of small aliquots (0.2 mL) which were filtered through silica gel (EtOAc eluent), evaporated and analyzed. After the reaction rate had significantly slowed (81 h, 55% conversion), and aliquot analysis showed high levels of enantiocontrol for the remaining alcohol (−)-4.1 (99.0% ee), the entire reaction mixture was filtered through a small column of silica gel (5×6 cm, EtOAc eluent). The filtrate was evaporated and purified by flash chromatography on silica gel (6:1→3:1 hexanes/EtOAc eluent) to provide ketone 4.2 (1.43 g, 54% yield) and alcohol (−)-4.1 (1.20 g, 44% yield, 99.0% ee) as white solids. The combination of both cycles provided alcohol (−)-4.1 (3.39 g, 68% yield, 99.0% ee).

Example 3

Oxidative Desymmetrization of Meso Diol

Reaction 5

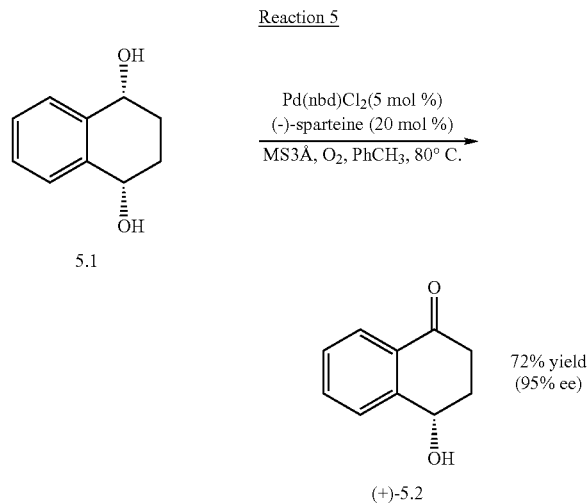

A 50 mL Schlenk flask equipped with a magnetic stir bar was charged with Molecular Sieves (MS3 Å, 625 mg) and flame-dried under vacuum. After cooling under dry $N_2$, Pd(nbd)Cl$_2$ (16.8 mg, 0.0625 mmol, 0.05 equiv) was added followed by toluene (12.5 mL), and (−)-sparteine (57 μL, 0.25 mmol, 0.20 equiv). The flask was vacuum evacuated and filled with $O_2$ (3×, balloon), and the reaction mixture was heated to 80° C. for 10 min. Diol 5.1 (205 mg, 1.25 mmol, 1.0 equiv; prepared as described in Yamada et al., *J. Org. Chem.* 64:9365 (1999)) was introduced and the reaction monitored by standard analytical techniques (TLC, GC, $^1$H-NMR, and HPLC) for % conversion and enantiomeric excess values. Upon completion of the reaction, the reaction mixture was filtered through a pad of SiO$_2$ (EtOAc eluent) and purified by column chromatography on SiO$_2$ (3:1→1:1 hexane/EtOAc eluent) to provide hydroxyketone (+)-5.2 as an oil (145 mg, 72% yield, 95% ee); $[\alpha]D^{23}$+19.6 (c 1.0, MeOH).

All patents, publications, and other published documents mentioned or referred to in this specification are herein incorporated by reference in their entirety.

It is to be understood that while the invention has been described in conjunction with the preferred specific embodiments hereof, the foregoing description, as well as the examples which are intended to illustrate and not limit the scope of the invention, it should be understood by those skilled in the art that various changes may be made and equivalents may be substituted without departing from the scope of the invention. Other aspects, advantages and modifications will be apparent to those skilled in the art to which the invention pertains.

Accordingly, the scope of the invention should therefore be determined with reference to the appended claims, along with the full range of equivalents to which those claims are entitled.

We claim:

1. A method of catalyzing an enantioselective oxidation reaction of an oxidizable, chiral organic compound composed of a racemic mixture of a first enantiomer and a second enantiomer, comprising:
   a) contacting the organic compound with:
      i) an oxidizing agent, and
      ii) a catalyst comprising a palladium composition and a selected enantiomer of a chiral ligand containing two or more tertiary nitrogen atoms that are separated by two or more linking atoms, thereby
   b) selectively oxidizing the first enantiomer of the organic compound so as to produce (i) an oxidized organic compound and (ii) a mixture of the first and second enantiomers in which the second enantiomer represents at least 50% of the mixture.

2. The method of claim 1 wherein the organic compound is selected from the group consisting of alcohols, thiols, amines and phosphines.

3. The method of claim 1 wherein the oxidizing agent is selected from the group consisting of molecular oxygen, benzoquinone, Cu (I) salts, and Cu (II) salts.

4. The method of claim 3 wherein the oxidizing agent is molecular oxygen.

5. The method of claim 1 wherein the oxidizing agent is used in a stoichiometric amount.

6. The method of claim 1 wherein said contacting is conducted in an organic solvent.

7. The method of claim 1 wherein the palladium composition is a palladium (II) complex.

8. The method of claim 7 wherein the palladium (II) complex is selected from the group consisting of Pd(OAc)$_2$, Pd$_2$(dibenzylideneacetone)$_3$, PdCl$_2$, Pd(CH$_3$CN$_2$)Cl$_2$, Pd(PhCN$_2$)Cl$_2$, [(allyl)PdCl]$_2$, PdCl$_2$ (cyclooctadiene), Pd(OCOCF$_3$), and Pd(norbornadiene)Cl$_2$.

9. The method of claim 1 where the second enantiomer represents at least 60% of the mixture.

10. The method of claim 9 where the second enantiomer represents at least 90% of the mixture.

11. The method of claim 1 wherein the organic compound is a secondary alcohol.

12. The method of claim 1 wherein the enantioselective oxidation reaction is an enantioselective Wacker-type cyclization reaction.

13. The method of claim 1 wherein the enantioselective oxidation reaction is an enantioselective aromatic oxidation reaction.

14. The method of claim 1 wherein the enantioselective oxidation reaction is the enantio-group differentiation of meso diols.

15. The method of claim 1 wherein the enantioselective oxidation reaction is an enantioselective oxidative [4+2] cycloaddition reaction.

16. The method of claim 1 wherein the enantioselective oxidation reaction is a C—C bond forming cyclization reaction.

17. The method of claim 1 wherein the enantioselective oxidation reaction is a cyclization reaction.

18. The method of claim 17 wherein the organic compound contains an olefin.

19. The method of claim 1 wherein the chiral ligand has the structure
$R^aR^aN$—$CR^bR^b$—$(X)_n$—$CR^bR^b$—$NR^aR^a$
wherein:
   each $R^a$ is independently selected from the group consisting of alkyl, cycloalkyl, cycloheteroalkyl, aryl, heteroaryl and silyl;
   X is —$CR^bR^b$— or a heteroatom;
   n is an integer from 0–2; and
   each $R^b$ is independently selected from the group consisting of hydrogen, alkyl, cycloalkyl, cycloheteroalkyl, aryl, heteroaryl and silyl, wherein two or more of $R^a$ and $R^b$ can be taken together to form one or more cyclic structures.

20. The method of claim 19 wherein n is 1 or 2.

21. The method of claim 19 wherein the chiral ligand is tetracyclic.

22. The method of claim 1 wherein the chiral ligand has the structure

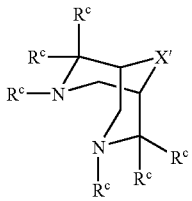

wherein: each $R^c$ is independently selected from the group consisting of hydrogen, alkyl, cycloalkyl, cycloheteroalkyl, aryl, heteroaryl and silyl, with the proviso that the $R^c$ substituents bound to the nitrogen atoms are other than hydrogen; and X' is selected from the group consisting of —O—, —S—, —N($R^d$)—, —C($R^d$)$_2$—, in which each $R^d$ is independently selected from the group consisting of hydrogen, alkyl, cycloalkyl, cycloheteroalkyl, aryl, heteroaryl and silyl, wherein two or more of $R^c$ and $R^d$ can be taken together to form one or more cyclic structures.

23. The method of claim 22 wherein X' is —C($R^d$)$_2$—.

24. The method of claim 19 wherein $R^a$ and $R^b$ are independently selected from the group consisting of branched, unbranched, and cyclic $C_1$–$C_{24}$ alkyl optionally substituted with at least one substituent.

25. The method of claim 24, wherein the at least one substituent is selected from hydroxyl, cyano, alkoxy, =O, =S, nitro, halogen, haloalkyl, heteroalkyl, amino, and sulfhydryl.

26. The method of claim 24 wherein $R^a$ and $R^b$ are independently selected from the group consisting of branched, unbranched, and cyclic $C_1$–$C_6$ alkyl optionally substituted with at least one substituent.

27. The method of claim 26 wherein the at least one substituent is selected from hydroxyl, cyano, alkoxy, =O, =S, nitro, halogen, haloalkyl, heteroalkyl, amino, and sulfhydryl.

28. The method of claim 1 wherein the chiral ligand is (−)-sparteine.

* * * * *